(12) United States Patent
Liu et al.

(10) Patent No.: US 12,741,114 B2
(45) Date of Patent: Sep. 22, 2026

(54) BREATHING GAS DELIVERY PIPE, NASAL CATHETER, AND VENTILATION THERAPY DEVICE

(71) Applicant: BMC MEDICAL CO., LTD., Beijing (CN)

(72) Inventors: Jiuzhong Liu, Tianjin (CN); Yunjing Chen, Tianjin (CN); Zhi Zhuang, Beijing (CN); Fang Zheng, Tianjin (CN); Anjun Zhang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 600 days.

(21) Appl. No.: 18/269,038

(22) PCT Filed: Nov. 12, 2021

(86) PCT No.: PCT/CN2021/130312
§ 371 (c)(1),
(2) Date: Jun. 22, 2023

(87) PCT Pub. No.: WO2022/134924
PCT Pub. Date: Jun. 30, 2022

(65) Prior Publication Data

US 2024/0042156 A1 Feb. 8, 2024

(30) Foreign Application Priority Data

Dec. 25, 2020 (CN) ........................ 202011562168.3

(51) Int. Cl.
*A61M 16/08* (2006.01)
*A61M 16/06* (2006.01)
(Continued)

(52) U.S. Cl.
CPC .... *A61M 16/0875* (2013.01); *A61M 16/0672* (2014.02); *A61M 16/1095* (2014.02);
(Continued)

(58) Field of Classification Search
CPC .. A61M 16/00; A61M 16/04; A61M 16/0461; A61M 16/0465; A61M 16/0475;
(Continued)

(56) References Cited

U.S. PATENT DOCUMENTS 5,357,948 A 10/1994 Eilentropp
5,623,922 A * 4/1997 Smith .............. A61M 16/0875 128/207.14

(Continued)

FOREIGN PATENT DOCUMENTS

CN 2659499 Y 12/2004
CN 203790406 U 8/2014

(Continued)

OTHER PUBLICATIONS

European Search Report for corresponding application EP21908924; Mail date Mar. 22, 2024.

(Continued)

*Primary Examiner* — Colin W Stuart
(74) *Attorney, Agent, or Firm* — CANTOR COLBURN LLP

(57) ABSTRACT

A breathing gas delivery pipe, a nasal catheter, and a ventilation therapy device, where the breathing gas delivery pipe is used for delivering gas to a patient interface, and includes a gas delivery pipe body including a gas delivery channel and a heat preservation structure used for preserving heat of the gas delivered in the gas delivery channel such that, the heat preservation structure preserves the heat of the gas delivery pipe body, so that the temperature drop in the gas delivery channel can be effectively slowed down or avoided, thereby a temperature drop of the gas delivered in the gas delivery channel is further slowed down or avoided, and the generation of condensed water in the gas delivery channel is avoided.

11 Claims, 10 Drawing Sheets

(51) Int. Cl.
*A61M 16/10* (2006.01)
*A61M 39/08* (2006.01)

(52) U.S. Cl.
CPC ....... *A61M 39/08* (2013.01); *A61M 2039/082* (2013.01); *A61M 2207/10* (2013.01)

(58) Field of Classification Search
CPC .......... A61M 16/0477; A61M 16/0486; A61M 16/0666; A61M 16/08; A61M 16/0145; A61M 16/0175; A61M 16/0672; A61M 16/0875; A61M 16/0808; A61M 16/0883; A61M 16/1095; A61M 25/00; A61M 25/0021; A61M 25/0026; A61M 39/08; A61M 2039/082
See application file for complete search history.

(56) References Cited

U.S. PATENT DOCUMENTS 5,640,951 A * 6/1997 Huddart .................. F16L 11/12 128/911
6,078,730 A * 6/2000 Huddart ................ A61M 16/08 219/536
6,536,428 B1 3/2003 Smith
9,295,801 B2 3/2016 Graham et al.
10,449,323 B2 10/2019 Cheung et al.
11,857,728 B1 * 1/2024 Schultz ............ A61M 16/0816
2002/0061375 A1 * 5/2002 Cartledge ............ F16L 11/045 428/36.9
2003/0059213 A1 3/2003 Mackie
2007/0283957 A1 * 12/2007 Schobel ............ A61M 16/0833 128/207.18
2008/0105257 A1 5/2008 Klasek et al.
2008/0251073 A1 * 10/2008 Jassell ............... A61M 16/1075 128/204.17
2009/0056715 A1 * 3/2009 Cortez, Jr. .......... A61M 16/109 128/203.26
2013/0112201 A1 5/2013 Graham
2015/0048530 A1 2/2015 Cheung et al.
2019/0009047 A1 1/2019 Dwyer
2020/0360642 A1 11/2020 Milne et al.

FOREIGN PATENT DOCUMENTS

CN 204804706 U 11/2015
CN 108310551 A 7/2018
CN 209108333 A 7/2019
CN 112604111 A 4/2021
CN 214807560 U 11/2021
CN 214807561 U 11/2021
WO 2004105848 A1 12/2004
WO 2005089847 A1 9/2005

OTHER PUBLICATIONS

International Search Report for corresponding application PCT/CN2021/130312 filed Nov. 12, 2021; Mail date Feb. 9, 2022.

* cited by examiner

BREATHING GAS DELIVERY PIPE, NASAL CATHETER, AND VENTILATION THERAPY DEVICE

CROSS REFERENCE TO RELATED APPLICATIONS

The present application claims for the benefits of the Chinese Patent Application No. 202011562168.3 filed on Dec. 25, 2020, the content of which is incorporated herein by reference.

FIELD

The present disclosure relates to the field of ventilation therapy devices, in particular to a breathing gas delivery pipe, a nasal catheter and a ventilation therapy device.

BACKGROUND

At present, ventilation therapy devices, such as ventilators and high-flow oxygen therapy devices, etc., are vital medical devices for patients with respiratory failure to maintain breathing, ensure ventilation, and save and prolong their lives. Ventilation therapy based on a ventilation therapy device is an effective way to replace the artificial autonomous ventilation function, and has widely applied in respiratory failure resulted from various reasons, anesthesia and respiratory control during major surgeries, respiratory support therapy, and first-aid and resuscitation. A nasal catheter used in such applications usually comprises a machine interface, a catheter, and a patient interface. The two ends of the catheter are connected to the machine interface and the patient interface respectively, so that warm and humid gas supplied by the machine can be delivered to the patient interface through the catheter, and then transferred to the respiratory tract of the patient through the patient interface.

In actual use, the catheter is usually exposed to the indoor air, consequently the warm and humid breathing gas transferred to the patient undergoes temperature drop in the catheter, accompanied by the generation of condensed water. Especially, in the case of a nasal catheter for children, the gas flow rate in the nasal catheter is very low (usually 2-25 L/min.), and the temperature drop of the gas in the catheter is great, thereby the condensed water is more obvious.

In addition, the ventilation cross-section of the catheter is usually circular, and when it is squeezed, and the catheter may be blocked easily if it is squeezed, e.g., flattened or bent. Such a blockage phenomenon may have impacts on the therapy of the patient if it is not discovered timely.

SUMMARY

An object of the present disclosure is to provide a breathing gas delivery pipe, which can reduce the temperature drop of the delivered gas, thereby reduces the generation of condensed water.

To attain the above object, the present disclosure provides a breathing gas delivery pipe, which is configured to deliver gas to a patient interface, and comprises a gas delivery pipe body, which comprises a gas delivery channel and a heat preservation structure for preserving the heat of the gas delivered in the gas delivery channel.

In this technical scheme, since the gas delivery pipe body comprises a heat preservation structure for preserving the gas delivered in the gas delivery channel, the heat preservation structure preserves the heat of the gas delivery pipe body, so that the temperature drop in the gas delivery channel can be effectively slowed down or avoided, thereby temperature drop of the gas delivered in the gas delivery channel is further slowed down or avoided, and the generation of condensed water in the gas delivery channel is avoided.

Furthermore, the heat preservation structure comprises a multi-layer heat preservation structure arranged in a radial direction.

Furthermore, the heat preservation structure can maintain a gas delivery clearance for gas delivery at a part of the gas delivery channel where the gas delivery channel is deformed when the gas delivery pipe body is squeezed and deformed at least partially.

Furthermore, the gas delivery pipe body comprises an inner pipe and an outer pipe fitted outside the inner pipe, with pipe support ribs arranged between the inner pipe and the outer pipe for keeping the inner pipe and the outer pipe spaced apart from each other, so that a heat preservation space is formed between the inner pipe and the outer pipe, wherein an internal channel inside the inner pipe serves as the gas delivery channel, and the heat preservation structure includes the heat preservation space.

Still furthermore, one radial end of each of the pipe support ribs is integrally formed with the inner pipe, and the other radial end of each of the pipe support ribs is integrally formed with the outer pipe;

or, one radial end of each of the pipe support ribs is integrally formed with one of the inner pipe and the outer pipe, and the other radial end of each of the pipe support ribs is not integrally formed with the other of the inner pipe and the outer pipe.

Furthermore, the heat preservation spacing is a closed cavity.

Still furthermore, an outer side wall of the heat preservation space is provided with a liquid discharge port and a side wall door capable of opening and closing the liquid discharge port.

Furthermore, the heat preservation structure comprises an electric heating wire arranged in the pipe wall of at least one of the inner pipe and the outer pipe.

Still furthermore, the electric heating wire extends linearly along the pipe or extends spirally around the pipe in an axial direction.

Furthermore, the heat preservation structure comprises a heat preservation layer filled inside the heat preservation space.

Furthermore, at least one of an inner side surface and an outer side surface of the heat preservation space is provided with an air space maintaining structure, which maintains an air space at a part of the outer pipe where the outer pipe is deformed when the outer pipe is squeezed and deformed at least partially.

Still furthermore, the air space maintaining structure comprises protrusions that protrude from at least one of the inner side surface and the outer side surface of the heat preservation space, wherein the protrusions can contact with opposite structures inside the heat preservation space so as to form the air space on at least one side of the protrusions in the circumferential direction when the outer pipe is squeezed and deformed.

Still furthermore, a plurality of protrusions are provided and arranged at an interval in the circumferential direction, and the opposite structures are a side surface of the heat preservation space opposite to the protrusions in the radial direction, or the opposite structures are opposite protrusions on the side surface of the heat preservation space opposite to the aforesaid protrusions in the radial direction.

Furthermore, the cross section of each of the protrusions is in a shape of spike, and spike side surfaces abutting the spike in the circumferential direction are concave arc-shaped surfaces.

In addition, optionally, the heat preservation structure comprises a heat preservation layer, the gas delivery pipe body comprises an inner pipe and an outer pipe that is supported and fitted outside the inner pipe via the heat preservation layer, and the internal channel inside the inner pipe serves as the gas delivery channel.

In addition, optionally, the gas delivery pipe body is a single-layer pipe body, with an electrical heating wire arranged inside the pipe wall of the single-layer pipe body, and/or a heat preservation layer wrapped on the outer surface of the single-layer pipe body.

Furthermore, the gas delivery pipe body comprises a gas delivery maintaining structure, which maintains a gas delivery clearance for gas delivery at a part of the gas delivery channel where the gas delivery channel is deformed when the gas delivery pipe body is squeezed and deformed at least partially.

Furthermore, the gas delivery maintaining structure is arranged on an inner channel surface of the gas delivery channel.

Still furthermore, the width dimension of the cross section of the gas delivery maintaining structure is reduced gradually in a radially inward direction.

Furthermore, the gas delivery maintaining structure comprises protrusions that protrude inward from the inner channel surface and extend axially along the gas delivery channel, wherein the protrusions can contact with opposite structures on the inner channel surface so as to form the gas delivery clearance on at least one side of the protrusions in the circumferential direction when the gas delivery pipe body is squeezed and deformed.

Still furthermore, the opposite structures are parts of the inner channel surface opposite to the protrusions in the radial direction.

Furthermore, a plurality of protrusions are provided and arranged at an interval in the circumferential direction.

Still furthermore, the opposite structures are protrusions on the inner channel surface opposite to the aforesaid protrusions in the radial direction.

Furthermore, the width dimension of the cross section of each of the protrusions is reduced gradually in the radially inward direction.

Still furthermore, the cross section of each of the protrusions is a shape of spike.

Still furthermore, at least one of the spike side surfaces abutting the spike in the circumferential direction is a concave arc-shaped surface.

Moreover, the present disclosure provides a nasal catheter comprising a gas source connecting terminal, a patient interface, and any breathing gas delivery pipe described above, wherein one end of the breathing gas delivery pipe is connected to the gas source connecting terminal, and the other end of the breathing gas delivery pipe is connected to the patient interface.

Finally, the present disclosure provides a ventilation therapy device comprising the nasal catheter described above.

Other features and advantages of the present disclosure will be detailed in the following embodiments.

BRIEF DESCRIPTION OF THE DRAWINGS

The accompanying drawings are provided herein to facilitate further understanding on the present disclosure and constitute a part of this document. They are used in conjunction with the following embodiments to explain the present disclosure, but are not intended to constitute any limitation to the present disclosure. In the figures.

DETAILED DESCRIPTION

Hereunder some embodiments of the present disclosure will be detailed with reference to the accompanying drawings. It should be understood that the embodiments described herein are only provided to describe and explain the present disclosure, but are not intended to constitute any limitation to the present disclosure.

Please see the breathing gas delivery pipes in different embodiments as shown in FIGS. 1-4, 6, 10, 11, 12, 13 and 16. The breathing gas delivery pipe provided by the present disclosure is configured to deliver gas to a patient interface, and comprises a gas delivery pipe body 1, which comprises a gas delivery channel 2 and a heat preservation structure for preserving the heat of the gas delivered in the gas delivery channel 2.

In the breathing gas delivery pipe, since the gas delivery pipe body 1 comprises a heat preservation structure for preserving the gas delivered in the gas delivery channel 2, the heat preservation structure preserves the heat of the gas delivery pipe body 1, so that the temperature drop in the gas delivery channel can be effectively slowed down or avoided, thereby temperature drop of the gas delivered in the gas delivery channel is further slowed down or avoided, and the generation of condensed water in the gas delivery channel is avoided.

Figure 1:
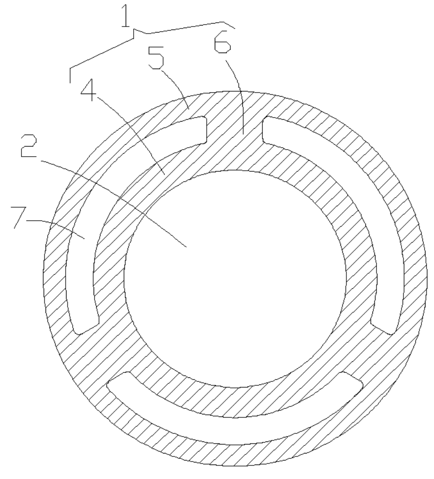
FIG. 1 is a schematic structural diagram of the cross section of a first breathing gas delivery pipe provided in an embodiment of the present disclosure.
Figure 2:
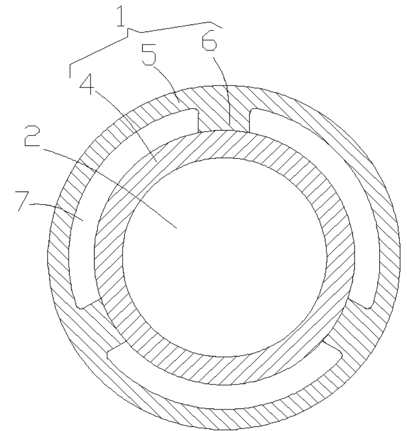
FIG. 2 is a schematic structural diagram of the cross section of a second breathing gas delivery pipe provided in an embodiment of the present disclosure.
Figure 3:
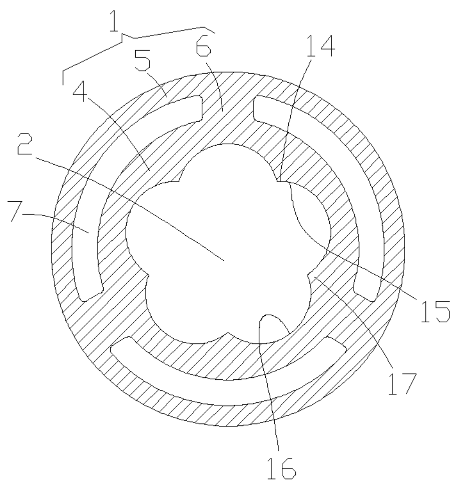
FIG. 3 is a schematic structural diagram of the cross section of a third breathing gas delivery pipe provided in an embodiment of the present disclosure.
Figure 4:
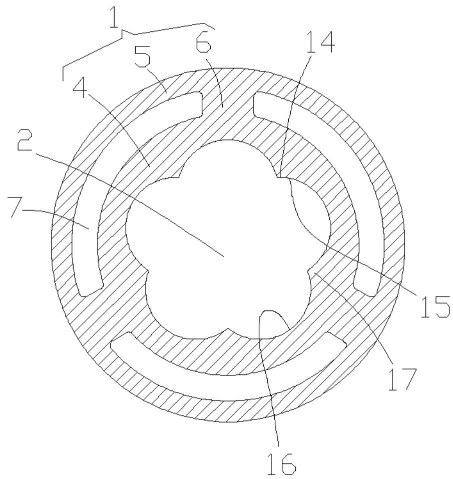
FIG. 4 is a schematic structural diagram of the cross section of a fourth breathing gas delivery pipe provided in an embodiment of the present disclosure.

In addition, in the breathing gas delivery pipe, the heat preservation structure may be an one-layer heat preservation structure, for example, the one-layer heat preservation space 7 as shown in FIGS. 1-3; alternatively, in order to improve the heat preservation effect further, the heat preservation structure may be a multi-layer heat preservation structure composed of multiple layers arranged in the radial direction, for example, the combination of an electrical heating wire 8 (one layer of heat preservation structure) and a heat preservation space 7 (another layer of heat preservation structure) as shown in FIG. 4. Of course, a multi-layer heat preservation structure is not limited to two layers; for example, a multi-layer heat preservation structure may be composed of three or four layers arranged in the radial direction sequentially.

In addition, the heat preservation structure of the breathing gas delivery pipe may further has a function of maintaining a gas delivery clearance 3 as described below, besides the heat preservation function, which is to say, the heat preservation structure can maintain a gas delivery clearance 3 for maintaining gas delivery at a part of the gas delivery channel 2 where the gas delivery channel 2 is deformed when the gas delivery pipe body 1 is squeezed and deformed at least partially. The gas delivery clearance 3 may be the gas delivery clearance as shown in FIGS. 8, 9, 14 and 15. In that way, since the heat preservation structure included in the gas delivery pipe body 1 can further improve the strength of the gas delivery pipe body 1 against squeezing and deformation, the degree of deformation of the gas delivery channel 2 can be decreased when the gas delivery pipe body 1 is squeezed and deformed at least partially, so as to avoid total blockage of the gas delivery channel 2 at the squeezed part. Thus, a gas delivery clearance 3 can be maintained at the deformed part of the gas delivery channel 2, and the gas delivered in the gas delivery channel 2 can be delivered through the gas delivery clearance 3, thereby adverse effects on the therapy of the patient are avoided.

Of course, in the breathing gas delivery pipe in the present disclosure, various types of heat preservation structures may be used. Different types of heat preservation structures that can be used in the present disclosure will be detailed below.

With a first type of heat preservation structure, as shown in FIGS. 1-4, 6 and 16, the gas delivery pipe body 1 comprises an inner pipe 4 and an outer pipe 5 fitted outside the inner pipe 4, with pipe support ribs 6 arranged between the inner pipe and the outer pipe to keep the inner pipe and the outer pipe spaced apart from each other, so that a heat preservation space 7 is formed between the inner pipe 4 and the outer pipe 5, wherein the internal channel inside the inner pipe 4 serves as the gas delivery channel 2, and the heat preservation structure includes the heat preservation space 7. Thus, in actual use, the heat preservation space 7 is sealed and filled with air. In that way, heat insulation and preservation effects attained since the coefficient of heat conductivity of air is much lower than that of the pipe walls and the air layer inside the heat preservation space 7 is not circulated substantially. The warm and humid breathing gas in the inner pipe 4 conducts heat to the air layer through the pipe wall of the inner tube 4, then the air layer conducts the heat to the pipe wall of the outer pipe 5, finally the heat is released to the atmosphere. Since the heat conductivity of air is very low and the air layer inside the heat preservation space 7 is not circulated substantially, the air layer will be heated up to a temperature close to the temperature of the breathing gas inside the inner pipe 4 after the breathing gas delivery pipe works for a while; thus, the temperature difference between the two sides of the pipe wall of the inner pipe 4 is decreased, the breathing gas has no great temperature drop at the pipe wall of the inner pipe 4, thereby a phenomenon of excessive condensed water generated as a result of great temperature drop of the temperature drop is avoided. For example, the breathing gas delivered through the breathing gas delivery pipe is at 37° C. at 25° C. room temperature. If a conventional single-layer catheter is used, a temperature difference of 12° C. will exist between the inner side and the outer side of the catheter, consequently there will be a great temperature difference between the inner wall of the catheter and the breathing gas, the breathing gas in contact with the inner wall will undergoes temperature drop, resulting in the generation of condensed water. In contrast, the heat preservation space 7 in an embodiment of the present application has an air layer therein. During use, the temperature of the air layer inside the heat preservation space 7 is between 25-37° C. (e.g., at a middle value of 31° C.). If the inner pipe is regarded as a conventional single-layer catheter, the function of the air layer in the heat preservation space 7 is equivalent to increasing the ambient temperature to 31° C., thereby the temperature difference between the two sides of the pipe wall of the inner pipe is decreased, the temperature at the inner side of the pipe wall of the inner pipe is increased, thereby the temperature drop of the breathing gas in contact with the inner side of the pipe wall of the inner pipe is decreased, and the generation of condensed water on the pipe wall of the inner pipe is mitigated.

In addition, the number of the pipe support ribs 6 may be determined according to the actual requirement. For example, 2, 3 or 4 pipe support ribs 6 may be used, as long as the inner pipe 4 and the outer pipe 5 can be kept spaced apart from each other.

In addition, as shown in FIG. 1, one radial end of the pipe support rib 6 is integrally formed with the inner pipe 4, and the other radial end of the pipe support rib 6 is integrally formed with the outer pipe 5. Thus, the forming is convenient, and the inner pipe 4 and the outer pipe 5 can be connected stably and reliably. Alternatively, as shown in FIG. 2, the pipe support rib 6 may be separated from the inner pipe 4 or the outer pipe 5, which is to say, one radial end of the pipe support rib 6 is integrally formed with one of the inner pipe 4 and the outer pipe 5, and the other radial end of the pipe support rib 6 is not integrally formed with the other of the inner pipe 4 and the outer pipe 5, but is assembled with the other of the inner pipe 4 and the outer pipe 5. Alternatively, the radial ends of the pipe support rib 6 are not integrally formed with the inner tube 4 and the outer tube 5 respectively, but are assembled with the inner pipe 4 and the outer pipe 5; for example, the pipe support rib 6 may be attached to the inner pipe 4, then the outer pipe 5 may be fitted around the pipe support rib 6 and the inner surface of the outer pipe 5 contacts with the pipe support rib 6.

In addition, the pipe support ribs 6 may be annular, and a plurality of annular pipe support ribs 6 are arranged at an interval in the length direction (axial direction) of the breathing gas delivery pipe. Alternatively, each pipe support rib 6 may have an axially extending rib segment in certain length, and a plurality of axially extending ribs may be arranged at an interval in the length direction (axial direction) of the breathing gas delivery pipe, or the axially extending rib segments may extend uninterruptedly from one end of the breathing gas delivery pipe to the other end of the breathing gas delivery pipe.

Figure 18:
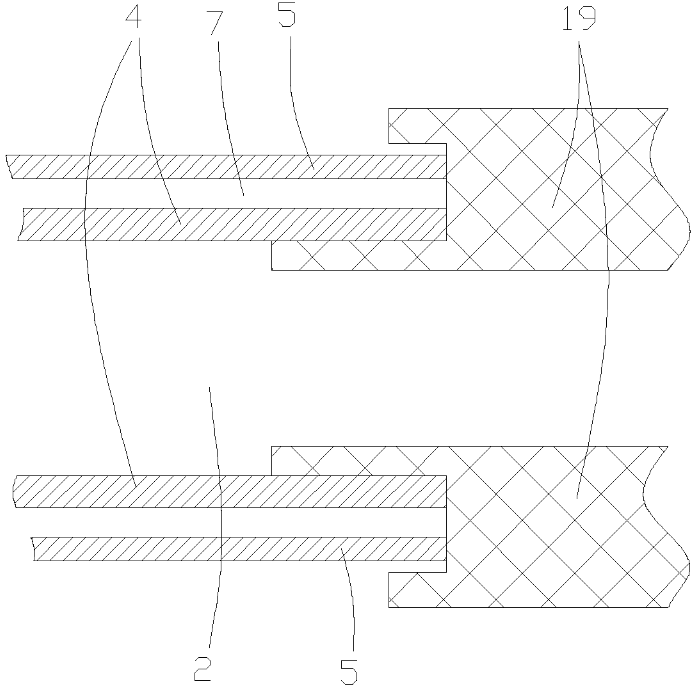
FIG. 18 is a schematic structural diagram of the breathing gas delivery pipe provided in an embodiment of the present disclosure, illustrating the connection of an end of the breathing gas delivery pipe with a connector.
Figure 19:
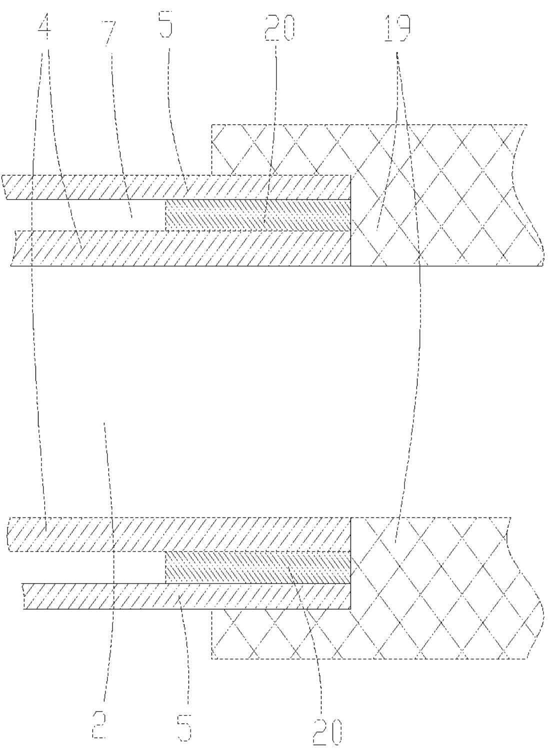
FIG. 19 is another schematic structural diagram of the breathing gas delivery pipe provided in an embodiment of the present disclosure, illustrating the connection of an end of the breathing gas delivery pipe with a connector.
Figure 20:
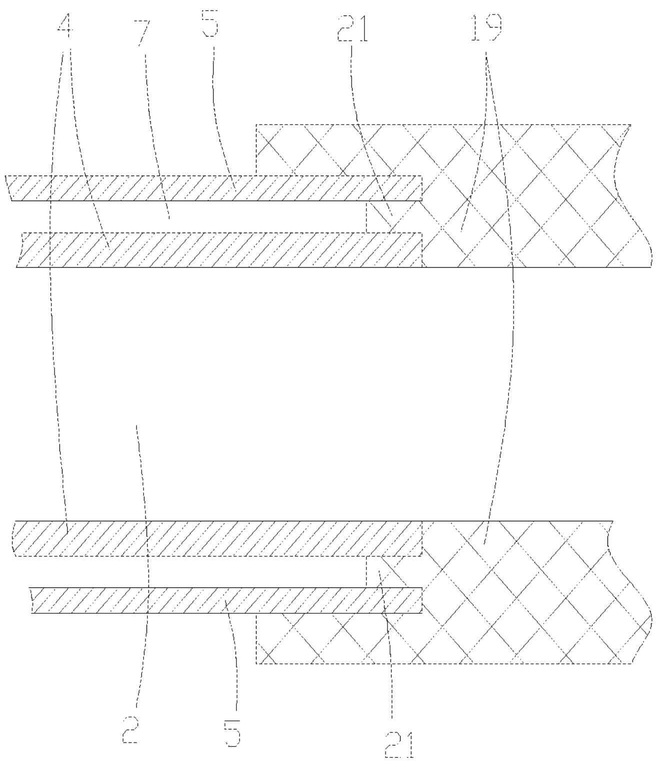
FIG. 20 is yet another schematic structural diagram of the breathing gas delivery pipe provided in an embodiment of the present disclosure, illustrating the connection of an end of the breathing gas delivery pipe with a connector.

In addition, in an embodiment of the breathing gas delivery pipe, the heat preservation space 7 may be an open space before the breathing gas delivery pipe is used, and may be connected and fitted with connectors 19 or plugs 20 (see FIGS. 18-20); for example, the heat preservation space 7 may be sealed by the end faces of the connectors 19 or by integral projections 21 on the end faces of the connectors 19, so that the heat preservation space 7 is encapsulated to form a sealed space. After the use, the breathing gas delivery pipe may be disconnected from the connectors 19 or plugs 20; at that point, any possible condensed water in the heat preservation space 7 may be removed.

Alternatively, in another embodiment of the breathing gas delivery pipe, the heat preservation space 7 is a closed cavity; for example, the end faces of the two axial ends of the outer pipe 5 may be connected to the inner pipe 4 via annular end walls so as to encapsulate the heat preservation space 7 into a closed cavity. During actual use, the two ends of the inner pipe 4 may be connected to the gas source connecting terminal and the patient interface respectively. Alternatively, the two ends of the breathing gas delivery pipe are connected with connectors 19 or plugs 20 respectively (see FIGS. 18-20) so as to encapsulate the heat preservation space 7 into a closed cavity. During actual use, the connectors 19 are connected to the gas source connecting terminal and/or the patient interface respectively, or the two ends of the breathing gas delivery pipe may be connected to the gas source connecting terminal and the patient interface respectively.

In addition, in actual use, condensed water may be generated in the closed heat preservation space 7. In view of that phenomenon, the outer side wall of the heat preservation space 7 is provided with a liquid discharge port and a side wall door capable of opening and closing the liquid discharge port. Thus, after use, the side wall door may be opened, and the condensed water in the heat preservation space 7 may be removed. The side wall door may be a connector or a plug 20, or any other door structure. For example, in the case that the pipe support ribs 6 are a plurality of annular pipe support ribs and arranged at an interval in the length direction (axial direction) of the breathing gas delivery pipe, the annular heat preservation space 7 between adjacent annular pipe support ribs will be an annular closed cavity. In that case, the annular pipe support ribs at the two axial ends of the annular closed cavity are inside the outer pipe 5 and can't be opened easily. To solve that problem, the pipe wall segment of the outer pipe 5 that forms the annular closed cavity may be provided with a liquid discharge port and a side wall door capable of opening and closing the liquid discharge port. After use, if condensed water exists in the annular closed cavity, the side wall door may be opened to discharge the condensed water; if there is no condensed water in the annular closed cavity, it is unnecessary to open the side wall door.

Figure 16:
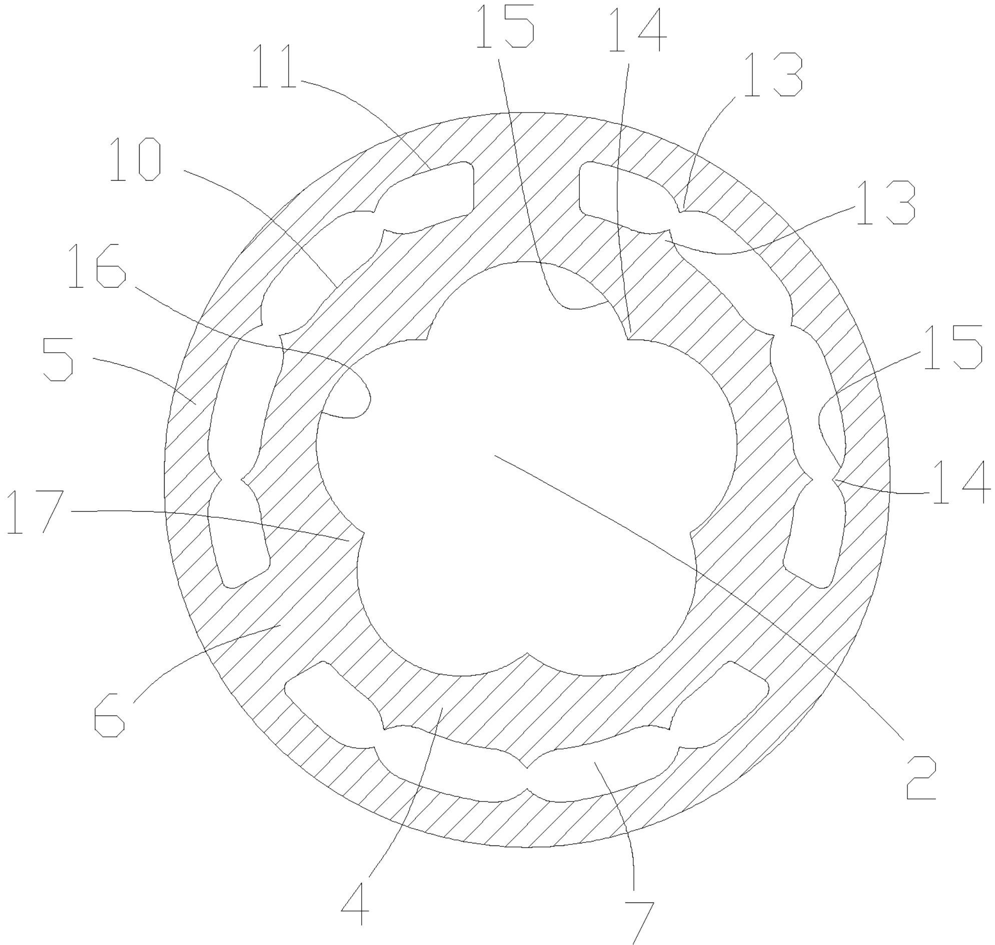
FIG. 16 is a schematic structural diagram of the cross section of a tenth breathing gas delivery pipe provided in an embodiment of the present disclosure.
Figure 17:
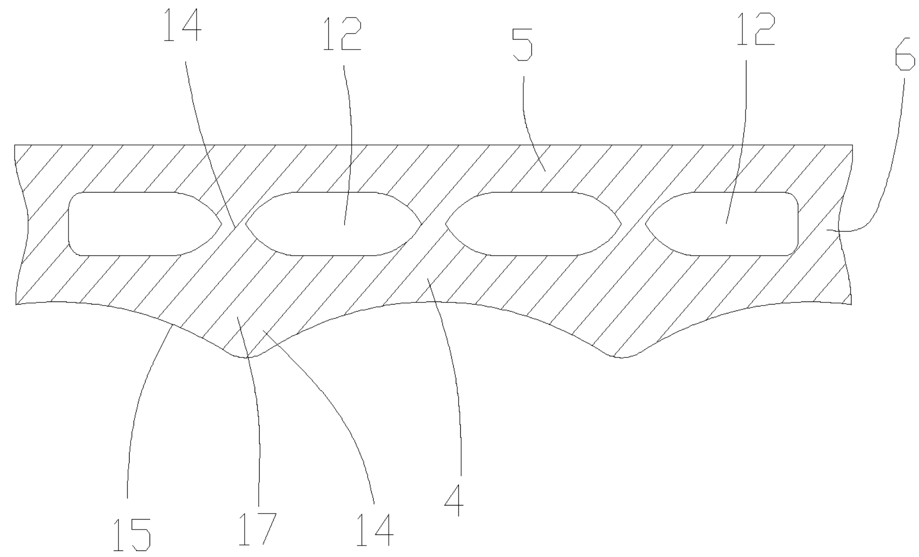
FIG. 17 is a schematic structural diagram of the deformed part of the breathing gas delivery pipe in FIG. 16 where an air space is maintained when the heat preservation space of the breathing gas delivery pipe is squeezed and deformed.

In addition, in an embodiment, as shown in FIGS. 16 and 17, at least one of the inner side surface 10 and the outer side surface 11 of the heat preservation space 7 is provided with an air space maintaining structure, which maintains an air space 12 at a part of the outer pipe 5 where the outer pipe 5 is squeezed and deformed at least partially. Thus, during actual use, if the outer pipe 5 is squeezed and deformed, the air space maintaining structure can maintain an air space 12 at the deformed part. For example, if the outer pipe 5 is compressed or bent under external force, the heat preservation space 7 between the inner pipe and the outer pipe will not be fully eliminated by the squeezing; instead, a part of the heat preservation space 7 between the inner pipe and the outer pipe stills forms an air space 12, and the air layer inside the air space 12 still attains heat insulation and heat preservation effects for the breathing gas inside the inner pipe, thereby the loss of the heat preservation performance can be prevented when the outer pipe 5 is squeezed or even the breathing gas delivery pipe is squeezed.

Of course, the air space maintaining structure may be in a variety of structural forms. For example, in a structural form of the air space maintaining structure, the air space maintaining structure is a supporting column, which is connected to the outer surface of the inner pipe and the inner surface of the outer pipe in the radial direction. In that way, an air space 12 will be formed at the two sides of the supporting column when the outer pipe is squeezed.

Alternatively, in another structural form of the air space maintaining structure, as shown in FIGS. 16 and 17, the air space maintaining structure comprises protrusions 13 that protrude from at least one of the inner side surface 10 and the outer side surface 11 of the heat preservation space 7, wherein the protrusions 13 may extend along the gas delivery channel 2 in the axial direction or extend in the circumferential direction to form circumferentially extending segments or annular protrusions. When the outer pipe 5 is squeezed and deformed, the protrusions 13 can contact with opposite structures inside the heat preservation space 7, so that an air space 12 is formed on at least one side of the protrusion 13 in the circumferential direction. For example, in FIG. 16, protrusions 13 protrude from the inner side surface 10 and the outer side surface 11. In FIG. 17, when the outer pipe 5 is squeezed and deformed, the protrusions 13 on the inner side surface 10 abut against the protrusions 13 on the outer side surface 11, thereby an air space 12 is formed on the sides in the circumferential direction. Alternatively, for example, protrusions 13 protrude from the inner side surface 10, but there is no protrusion 13 on the outer side surface 11. When the outer pipe 5 is squeezed and deformed, the protrusions 13 on the inner side 10 abut against the outer side surface 11, thereby an air space 12 is formed on the sides in the circumferential direction.

Of course, one or more protrusions 13 may be provided. For example, in an embodiment, a plurality of protrusions 13 are provided and arranged at an interval in the circumferential direction, and the opposite structures are the side surface of the heat preservation space 7 opposite to the protrusions 13 in the radial direction. For example, there is no protrusion 13 on the inner side surface 10, and protrusions 13 protrude from the outer side surface 11. When the outer pipe 5 is squeezed and deformed, the protrusions 13 on the outer side surface 11 abut against the inner side surface 10, which serves as opposite structures here, thereby an air space 12 is formed on the sides in the circumferential direction. Alternatively, as shown in FIG. 17, the opposite structures are opposite protrusions 13 protruding from the side surface of the heat preservation space 7 opposite to the protrusions 13 in the radial direction. The protrusions 13 that come into contact with each other can increase the volume of the air space 12 and improve the heat preservation performance. That is to say, there are protrusions 13 on the inner side surface 10 and the outer side surface 11. In FIG. 17, when the outer pipe 5 is squeezed and deformed, the protrusions 13 on the inner side surface 10 abut against the opposite protrusions 13 on the outer side surface 11, thereby an air space 12 is formed on the sides in the circumferential direction.

Of course, alternatively, the opposite structures may be other bosses or bumps other than protrusions 13 on the inner side surface 10 or the outer side surface 11.

Moreover, the cross section of each of the protrusions 13 may be in a variety of shapes, such as a rectangle. That is to say, the protrusions 13 may have the same dimension in the radial direction. For example, the protrusions 13 may be cylinders.

In an embodiment, in order to minimize the space occupation of the protrusions 13 in the heat preservation space 7 and improve the heat preservation performance, the width dimension of the cross section of each protrusion 13 may be reduced gradually in a radially inward direction. For example, the cross section of each protrusion 13 may be in a trapezoidal, triangular or semi-circular shape, etc.

In addition, as shown in FIG. 16, the cross section of each of the protrusions 13 is in a shape of spike 14, and spike side surfaces 15 abutting the spike 14 in the circumferential direction are concave arc-shaped surfaces. Thus, the spikes 14 can reduce the space occupation in the heat preservation space 7 in itself, and the concave arc-shaped surfaces can further reduce the space occupation of the spikes 14 in the heat preservation space 7.

Figure 6:
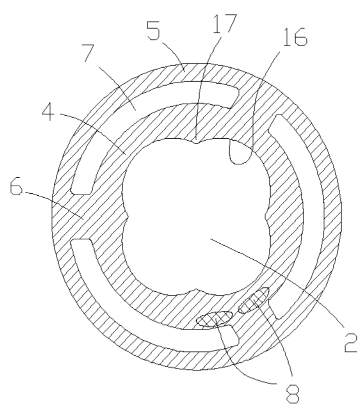
FIG. 6 is a schematic structural diagram of the cross section of a fifth breathing gas delivery pipe provided in an embodiment of the present disclosure.

Moreover, as shown in FIGS. 4 and 6, in an embodiment, during actual use, the heat preservation space is only used for heat preservation. In situations where the heat dissipation is severe owing to an extremely low room temperature or an extremely high indoor air flow rate, the heat preservation space 7 may have severe heat loss, consequently the temperature drop of the breathing gas inside the inner pipe is still great. In view of that problem, the heat preservation structure may include an electrical heating wire 8, which is arranged inside the pipe wall of at least one of the inner pipe 4 and the outer pipe 5; for example, as shown in FIGS. 4 and 6, the electrical heating wire 8 is arranged inside the pipe wall of the inner pipe 4, thereby a two-layer heat preservation structure is formed by the electrical heating wire 8 and the heat preservation space 7. The inner pipe with the electrical heating wire and the heat preservation space 7 attain a synergetic effect, i.e., not only heat insulation and heat preservation functions are achieved, but also the breathing gas inside the inner pipe can be heated to an appropriate temperature for the patient, and the generation of condensed water can be prevented. Of course, alternatively, the electrical heating wire 8 may be arranged inside the pipe wall of the outer pipe or inside the pipe walls of both the inner pipe and the outer pipe.

Figure 5:
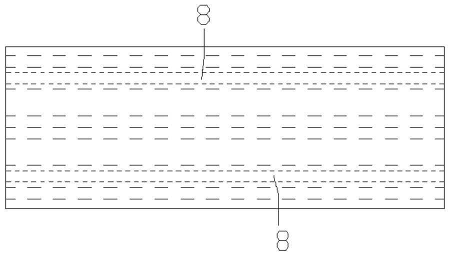
FIG. 5 is a schematic structural diagram of a part of the breathing gas delivery pipe in FIG. 4 in a side view.
Figure 7:
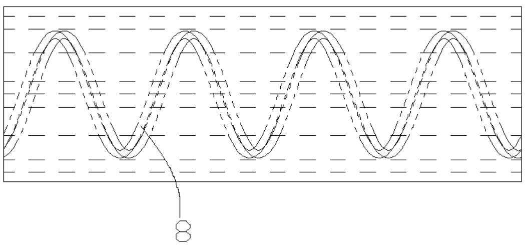
FIG. 7 is a schematic structural diagram of a part of the breathing gas delivery pipe in FIG. 6 in a side view.

In addition, the electrical heating wire 8 extends linearly in the axial direction, so that it can be arranged conveniently, as shown in FIG. 5; alternatively, the electrical heating wire 8 is wound on the pipe (inner pipe or outer pipe) and extends spirally, as shown in FIG. 7, so as to increase the heating area of the electrical heating wire. Of course, alternatively, the electrical heating wire 8 may extends from one end of the breathing gas delivery pipe to the other end of the breathing gas delivery pipe in an inclined form, rather than extending spirally.

Figure 11:
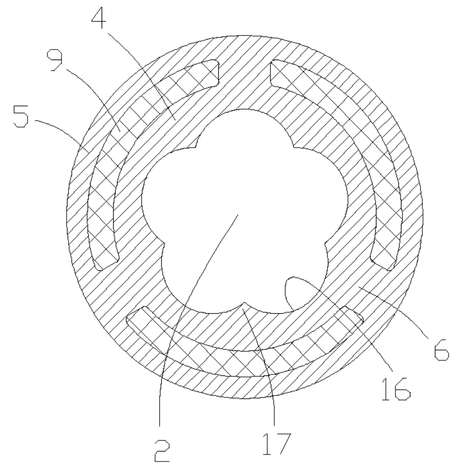
FIG. 11 is a schematic structural diagram of the cross section of a seventh breathing gas delivery pipe provided in an embodiment of the present disclosure.

In an optional embodiment, as shown in FIG. 11, the heat preservation structure comprises a heat preservation layer 9, which is filled inside the heat preservation space 7. Thus, the heat preservation layer 9 can improve the heat preservation performance. The heat preservation layer 9 may be made of a soft heat insulating material, which has no significant adverse effect on the flexibility of the breathing gas delivery pipe.

Figure 12:
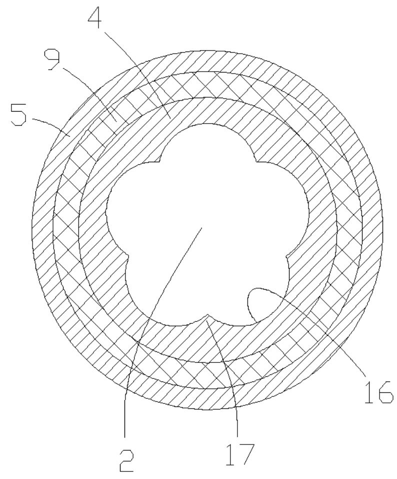
FIG. 12 is a schematic structural diagram of the cross section of an eighth breathing gas delivery pipe provided in an embodiment of the present disclosure.

In addition, in a second type of heat preservation structure, as shown in FIG. 12, the heat preservation structure comprises a heat preservation layer 9, the gas delivery pipe body 1 comprises an inner pipe 4 and an outer pipe 5 that is supported and fitted outside the inner pipe 4 via the heat preservation layer 9, and the internal channel inside the inner pipe 4 serves as the gas delivery channel 2. The heat preservation layer 9 can improve the heat preservation performance. The heat preservation layer 9 may be made of a soft heat insulating material, which has no significant adverse effect on the flexibility of the breathing gas delivery pipe.

Figure 10:
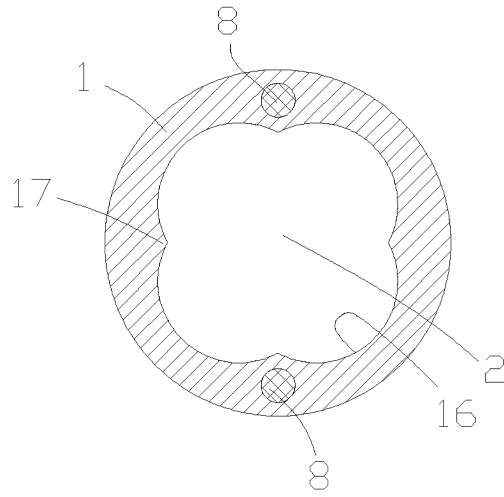
FIG. 10 is a schematic structural diagram of the cross section of a sixth breathing gas delivery pipe provided in an embodiment of the present disclosure.

In addition, in a third type of heat preservation structure, as shown in FIG. 10, the gas delivery pipe body 1 is a single-layer pipe body, with an electrical heating wire 8 arranged inside the pipe wall of the single-layer pipe body, wherein the electrical heating wire 8 may extend linearly in the axial direction so that it can be arranged conveniently, or the electrical heating wire 8 may be wound on the single-layer pipe body and extend spirally so as to increase the heating area of the electrical heating wire.

Figure 13:
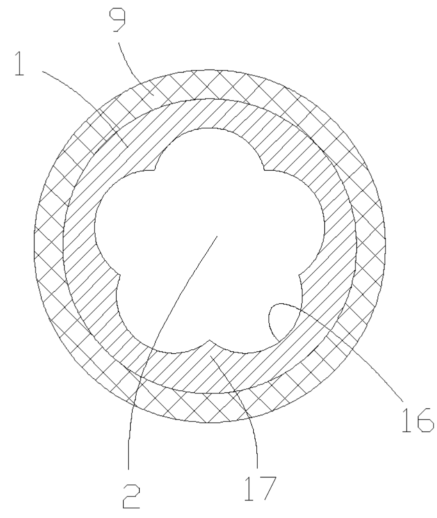
FIG. 13 is a schematic structural diagram of the cross section of a ninth breathing gas delivery pipe provided in an embodiment of the present disclosure.

In addition, in a fourth type of heat preservation structure, as shown in FIG. 13, a heat preservation layer 9 is wrapped on the outer surface of a single-layer pipe body. The heat preservation layer 9 can improve the heat preservation performance. The heat preservation layer 9 may be made of a soft heat insulating material, which has no significant adverse effect on the flexibility of the breathing gas delivery pipe. Alternatively, an electrical heating wire 8 is arranged inside the pipe wall of the single-layer pipe body, and a heat preservation layer 9 is wrapped on the outer surface of the single-layer pipe body.

In addition, in the embodiments shown in FIGS. 3, 4, 6, 8-9, 10 and 11-16, the gas delivery pipe body 1 comprises a gas delivery maintaining structure, which maintains a gas delivery clearance 3 at a part of the gas delivery channel 2 where the gas delivery channel 2 is deformed when the gas delivery pipe body 1 is squeezed and deformed at least partially. The gas delivery clearance 3 can prevent the deformed part from blocked completely under the squeezing. Thus, the gas delivered in the gas delivery channel 2 can be delivered through the gas delivery clearance 3, and adverse effects on the therapy of the patient can be avoided.

In an embodiment, the gas delivery maintaining structure may comprise any heat preservation structure described above, such as an electrical heating wire or a heat preservation layer, etc., which can further improve the strength of the gas delivery pipe body 1 against squeezing and deformation. For example, a heat preservation space 7 may be arranged between the inner pipe and the outer pipe, or a heat preservation layer may be arranged inside the heat preservation space 7, etc., so as to further improve the strength of the gas delivery pipe body 1 against squeezing and deformation.

In an embodiment, the gas delivery maintaining structure may be reinforcing structure formed on the outer surface of the gas delivery pipe body 1, such as spiral ribs. The reinforcing structures can further improve the strength of the gas delivery pipe body 1 against squeezing and deformation, so that the degree of deformation of the gas delivery channel 2 can be decreased when the gas delivery pipe body 1 is squeezed and deformed at least partially, so as to avoid total blockage of the gas delivery channel 2 at the squeezed part. Thus, a gas delivery clearance 3 is formed at the deformed part, and the gas delivered inside the gas delivery channel 2 can be delivered through the gas delivery clearance 3, thereby adverse effects on the therapy of the patient are avoided.

In an embodiment, the gas delivery maintaining structure is arranged on an inner channel surface 16 of the gas delivery channel 2. In that way, the gas delivery maintaining structure on the inner channel surface 16 can form the gas delivery clearance 3 inside the gas delivery channel more directly.

The gas delivery maintaining structure may have the same dimension in the radial direction. Alternatively, in order to further reduce the space occupation inside the gas delivery channel 2 so as to minimize the adverse effect on the gas delivery, the width dimension of the cross section of the gas delivery maintaining structure is reduced gradually in the radial direction. Thus, since the width dimension is reduced gradually, the space occupation inside the gas delivery channel 2 can be minimized while the gas delivery maintaining structure is connected with the inner channel surface 16 stably and reliably through great contact area.

In addition, in an embodiment, the gas delivery maintaining structure comprises supporting bars, the two ends of each of which are connected to opposite parts of the inner channel surface 16 respectively. Alternatively, the gas delivery maintaining structure comprises protrusions 17 that protrude inward from the inner channel surface 16 and extend along the gas delivery channel 2 in the axial direction. Thus, when the gas delivery pipe body 1 is squeezed and deformed, as shown in FIGS. 8, 9, 14 and 15, the protrusions 17 can contact with opposite structures on the inner channel surface 16, so that gas delivery clearance 3 is formed on at least one side of the protrusions 17 in the circumferential direction. Compared with the supporting bars, the protrusions 17 can effectively reduce the space occupation in the gas delivery channel 2.

Figure 9:
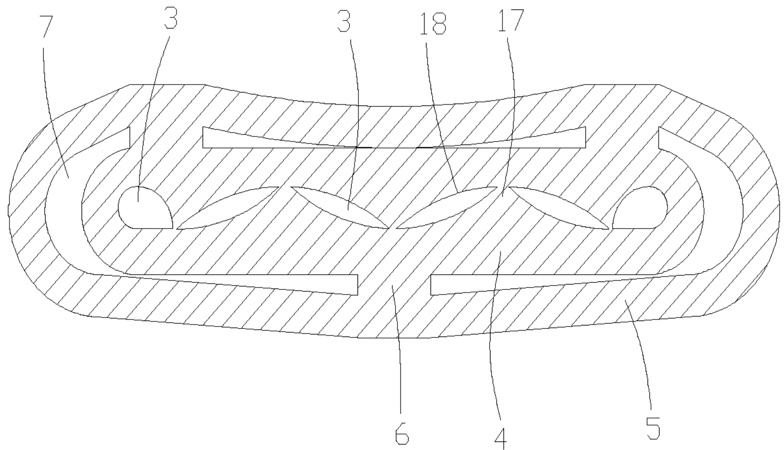
FIG. 9 is another schematic structural diagram of the breathing gas delivery pipe in FIG. 3 in a squeezed state.
Figure 15:
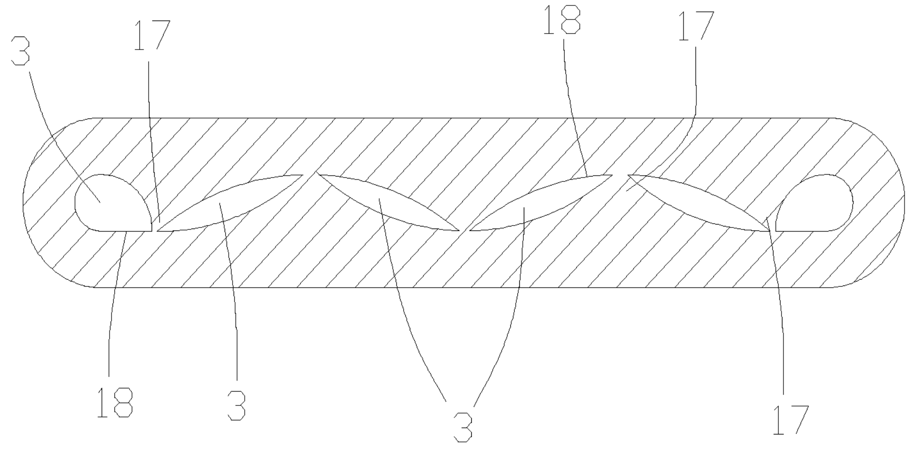
FIG. 15 is another schematic structural diagram of the breathing gas delivery pipe having a gas delivery clearance for maintaining gas delivery at a part of deformation when the breathing gas delivery pipe is squeezed and deformed according to the embodiments of the present disclosure.

Moreover, a variety of types of opposite structures may be used. For example, in a type of opposite structures, the opposite structures are inner surface parts 18 of the inner channel surface 16 opposite to the protrusions 17 in the radial direction. As shown in FIGS. 9 and 15, in that case, no matter one or more protrusions 17 (e.g., two, three, four or five protrusions) are provided, the protrusion(s) 17 will contact with the inner surface part(s) 18 when the gas delivery pipe body is squeezed, e.g., collapsed or bent, so that gas delivery clearance 3 is formed on at least one side of the protrusion(s) 17 in the circumferential direction.

Of course, one or more protrusions 17 may be provided, and a plurality of protrusions 17 may be arranged at an interval in the circumferential direction, so that the gas delivery maintaining capability of the gas delivery pipe body 1 can be improved effectively. For example, no matter which part of the gas delivery pipe body 1 is squeezed, gas delivery clearance 3 can be formed by the protrusions 17 at the part.

Figure 8:
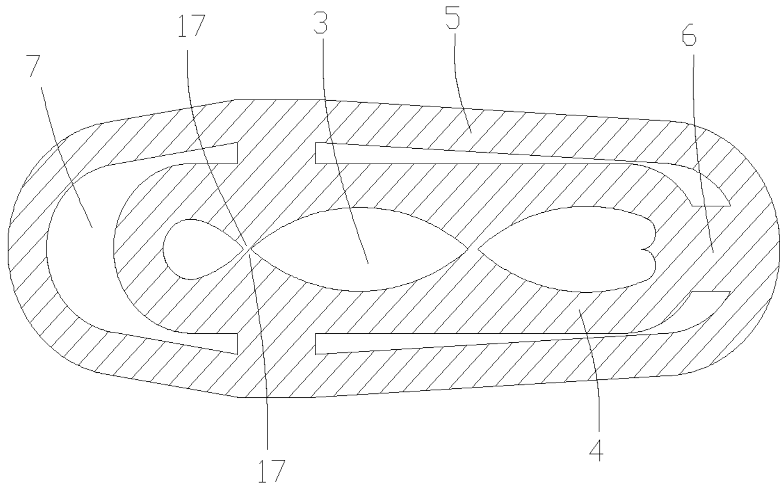
FIG. 8 is a schematic structural diagram of the breathing gas delivery pipe in FIG. 3 in a squeezed state.
Figure 14:
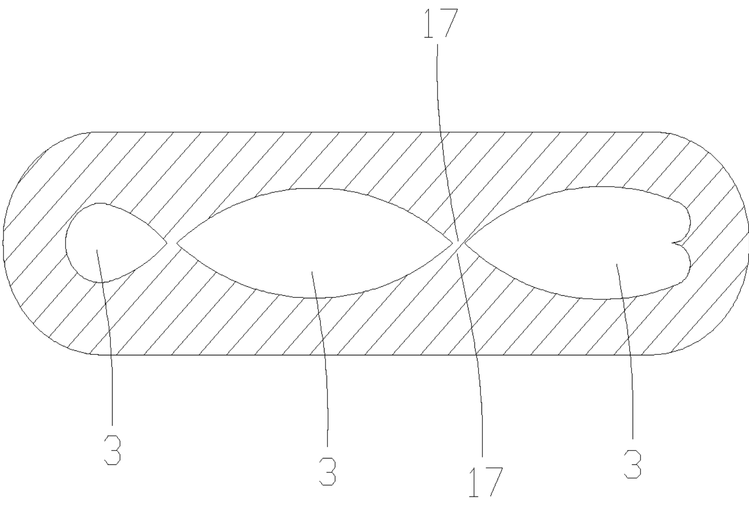
FIG. 14 is a schematic structural diagram of the breathing gas delivery pipe having a gas delivery clearance for maintaining gas delivery at a part of deformation when the breathing gas delivery pipe is squeezed and deformed according to the embodiments of the present disclosure.

Accordingly, in another type of opposite structures, as shown in FIGS. 8 and 14, a plurality of protrusions 17 are provided and arranged at an interval in the circumferential direction, and the opposite structures are opposite protrusions 17 on the inner channel surface 16 opposite to the aforesaid protrusions 17 in the radial direction. In that way, when the gas delivery pipe body is squeezed, e.g., collapsed or bent, the protrusions 17 come into contact with each other, so that gas delivery clearance 3 is formed on at least one side of the protrusions 17 in the circumferential direction, and the protrusions 17 in contact with each other can increase the gas delivery maintaining space 3 and improve the gas delivery maintaining capability.

Of course, alternatively, the opposite structures may be other bosses or bumps other than protrusions 17 formed on the inner channel surface 16.

Moreover, the cross section of each of the protrusions 17 may be in a variety of shapes, such as a rectangle. That is to say, the protrusions 17 have the same dimension in the radial direction. In an embodiment, in order to minimize the space occupation of the protrusions 17 inside the gas delivery channel 2 and improve the gas delivery maintaining capability, the width dimension of the cross section of each protrusion 17 is gradually reduced in the radially inward direction. For example, the cross section of each protrusion 17 may be in a trapezoidal, triangular or semi-circular shape, etc.

In addition, in an embodiment, as shown in FIG. 16, the cross section of each protrusion 17 is in the shape of a spike 14. Thus, the spike 14 can reduce the space occupation inside the gas delivery channel 2 in itself.

Moreover, at least one of the spike side surfaces 15 abutting the spike 14 in the circumferential direction is a concave arc-shaped surface. Thus, the spike 14 can reduce the space occupation inside the gas delivery channel 2 in itself, and the concave arc-shaped surface can further decrease the space occupation inside the gas delivery channel 2, thereby the gas delivery maintaining capability can be further improved at the deformed part.

Moreover, the present disclosure provides a nasal catheter comprising a gas source connecting terminal, a patient interface, and any breathing gas delivery pipe described above, wherein one end of the breathing gas delivery pipe is connected to the gas source connecting terminal, and the other end of the breathing gas delivery pipe is connected to the patient interface. In that way, the overall performance of the nasal catheter is improved.

Finally, the present disclosure provides a ventilation therapy device comprising the nasal catheter described above. The ventilation therapy device may be a ventilator or a high-flow oxygen therapy device.

While some preferred embodiments of the present disclosure are described above with reference to the accompanying drawings, the present disclosure is not limited to the details in those embodiments. Those skilled in the art can make various simple modifications and variations to the technical scheme of the present disclosure, without departing from the technical concept of the present disclosure.

However, all these simple modifications and variations shall be deemed as falling in the scope of protection of the present disclosure.

In addition, it should be noted that the specific technical features described in the above embodiments may be combined in any appropriate form, provided that there is no conflict among them. To avoid unnecessary repetition, various possible combinations are not described specifically in the present disclosure.

Moreover, different embodiments of the present disclosure may also be combined freely as required, as long as the combinations don't deviate from the ideal of the present disclosure. However, such combinations shall also be deemed as being disclosed in the present disclosure.

The invention claimed is:

1. A breathing gas delivery pipe configured to deliver gas to a patient interface, comprising a gas delivery pipe body (1), which comprises an inner pipe (4) defining a gas delivery channel (2) therein and an outer pipe (5) fitted outside the inner pipe (4), with pipe support ribs (6) arranged between the inner pipe (4) and the outer pipe (5) for keeping the inner pipe (4) and the outer pipe (5) spaced apart from each other, so that a heat preservation space (7) is formed between the inner pipe (4) and the outer pipe (5), wherein an electric heating wire (8) is arranged in a pipe wall of at least one of the inner pipe (4) and the outer pipe (5), and wherein an inner side surface (10) of the heat preservation space (7) is provided with protrusions (13) that are arranged at an interval in the circumferential direction and protrude from the inner side surface (10), and an outer side surface (11) of the heat preservation space (7) is provided with opposite protrusions (13) that protrude from the outer side surface (11), the protrusions (13) contact with the opposite protrusions (13) so as to form an air space (12) on at least one side of the protrusions (13) in the circumferential direction when the outer pipe (5) is squeezed and deformed.

2. The breathing gas delivery pipe of claim 1, wherein one radial end of each of the pipe support ribs (6) is integrally formed with the inner pipe (4), and the other radial end of each of the pipe support ribs (6) is integrally formed with the outer pipe (5); or, one radial end of each of the pipe support ribs (6) is integrally formed with one of the inner pipe (4) and the outer pipe (5), and the other radial end of each of the pipe support ribs (6) is not integrally formed with the other of the inner pipe (4) and the outer pipe (5).

3. The breathing gas delivery pipe of claim 1, wherein the heat preservation space (7) is a closed cavity.

4. The breathing gas delivery pipe of claim 1, wherein the electric heating wire (8) extends linearly along the inner pipe (4) or extends spirally around the gas delivery channel (2) in an axial direction.

5. The breathing gas delivery pipe of claim 1, wherein the cross section of each of the protrusions (13) is in a shape of spike (14), and spike side surfaces (15) abutting the spike (14) in the circumferential direction are concave arc-shaped surfaces.

6. The breathing gas delivery pipe of claim 1, wherein the gas delivery pipe body (1) comprises a gas delivery maintaining structure, which maintains a gas delivery clearance (3) for gas delivery at a part of the gas delivery channel (2) where the gas delivery channel (2) is deformed when the gas delivery pipe body (1) is squeezed and deformed at least partially.

7. The breathing gas delivery pipe of claim 6, wherein the gas delivery maintaining structure comprises protrusions (17) that protrude inward from an inner channel surface (16) of the gas delivery channel (2) and extend axially along the gas delivery channel (2), wherein the protrusions (17) of the gas delivery maintaining structure can contact with opposite structures on the inner channel surface (16) so as to form the gas delivery clearance (3) on at least one side of the protrusions (17) of the gas delivery maintaining structure in the circumferential direction when the gas delivery pipe body (1) is squeezed and deformed.

8. The breathing gas delivery pipe of claim 7, wherein the opposite structures are parts (18) of the inner channel surface (16) opposite to the protrusions (17) of the gas delivery maintaining structure in the radial direction.

9. The breathing gas delivery pipe of claim 7, wherein a plurality of protrusions (17) are provided and arranged at an interval in the circumferential direction.

10. A nasal catheter comprising a gas source connecting terminal, a patient interface, and a breathing gas delivery pipe, wherein one end of the breathing gas delivery pipe is connected to the gas source connecting terminal, and the other end of the breathing gas delivery pipe is connected to the patient interface and wherein the breathing gas delivery pipe comprises a gas delivery pipe body (1), which comprises an inner pipe (4) defining a gas delivery channel (2) therein and an outer pipe (5) fitted outside the inner pipe (4), with pipe support ribs (6) arranged between the inner pipe (4) and the outer pipe (5) for keeping the inner pipe (4) and the outer pipe (5) spaced apart from each other, so that a heat preservation space (7) is formed between the inner pipe (4) and the outer pipe (5), wherein an electric heating wire (8) is arranged in a pipe wall of at least one of the inner pipe (4) and the outer pipe (5), and wherein an inner side surface (10) of the heat preservation space (7) is provided with protrusions (13) that are arranged at an interval in the circumferential direction and protrude from the inner side surface (10), and an outer side surface (11) of the heat preservation space (7) is provided with opposite protrusions (13) that protrude from the outer side surface (11), the protrusions (13) contact with the opposite protrusions (13) so as to form an air space (12) on at least one side of the protrusions (13) in the circumferential direction when the outer pipe (5) is squeezed and deformed.

11. A ventilation therapy device comprising a nasal catheter, wherein the nasal catheter comprises a gas source connecting terminal, a patient interface, and a breathing gas delivery pipe, wherein one end of the breathing gas delivery pipe is connected to the gas source connecting terminal, and the other end of the breathing gas delivery pipe is connected to the patient interface and wherein the breathing gas delivery pipe comprises a gas delivery pipe body (1), which comprises an inner pipe (4) defining a gas delivery channel (2) therein and an outer pipe (5) fitted outside the inner pipe (4), with pipe support ribs (6) arranged between the inner pipe (4) and the outer pipe (5) for keeping the inner pipe (4) and the outer pipe (5) spaced apart from each other, so that a heat preservation space (7) is formed between the inner pipe (4) and the outer pipe (5), wherein an electric heating wire (8) is arranged in a pipe wall of at least one of the inner pipe (4) and the outer pipe (5), and wherein an inner side surface (10) of the heat preservation space (7) is provided with protrusions (13) that are arranged at an interval in the circumferential direction and protrude from the inner side surface (10), and an outer side surface (11) of the heat preservation space (7) is provided with opposite protrusions (13) that protrude from the outer side surface (11), the protrusions (13) contact with the opposite protrusions (13) so as to form an air space (12) on at least one side of the protrusions (13) in the circumferential direction when the outer pipe (5) is squeezed and deformed.

* * * * *